(12) United States Patent
Yoda (10) Patent No.: US 11,395,609 B2
(45) Date of Patent: Jul. 26, 2022

(54) SEMICONDUCTOR DEVICE AND SENSOR MODULE

(71) Applicant: SHINKO ELECTRIC INDUSTRIES CO., LTD., Nagano (JP)

(72) Inventor: Atsuto Yoda, Nagano (JP)

(73) Assignee: SHINKO ELECTRIC INDUSTRIES CO., LTD., Nagano (JP)

( * ) Notice: Subject to any disclaimer, the term of this patent is extended or adjusted under 35 U.S.C. 154(b) by 612 days.

(21) Appl. No.: 16/385,043

(22) Filed: Apr. 16, 2019

(65) Prior Publication Data
US 2019/0320950 A1 Oct. 24, 2019

(30) Foreign Application Priority Data
Apr. 20, 2018 (JP) .............................. JP2018-081119

(51) Int. Cl.
*A61B 5/145* (2006.01)
*A61B 5/00* (2006.01)

(52) U.S. Cl.
CPC ........ *A61B 5/14542* (2013.01); *A61B 5/6826* (2013.01)

(58) Field of Classification Search
CPC .............. A61B 5/14542; A61B 5/6826; A61B 2562/164; A61B 2562/166; A61B 5/14552
See application file for complete search history.

(56) References Cited

U.S. PATENT DOCUMENTS

| 5,520,177 A * | 5/1996 | Ogawa ............... A61B 5/14552 600/323 |
| 2007/0123756 A1 | 5/2007 | Kitajima et al. |
| 2012/0119377 A1* | 5/2012 | Muramatsu ....... H01L 23/49822 257/774 |
| 2015/0327809 A1 | 11/2015 | Tateda et al. |

FOREIGN PATENT DOCUMENTS

| JP | H05-317295 A | 12/1993 |
| JP | H07-043295 A | 2/1995 |
| JP | H09-276254 A | 10/1997 |

(Continued)

OTHER PUBLICATIONS

Japanese Office Action with English translation dated Dec. 14, 2021, 10 pages.

*Primary Examiner* — Allen Porter
*Assistant Examiner* — Abid A Mustansir
(74) *Attorney, Agent, or Firm* — Rankin, Hill & Clark LLP (57) ABSTRACT

A sensor module includes a ring-shaped member; and a semiconductor device that is provided on the ring-shaped member. The semiconductor device includes: a wiring substrate that has flexibility; and electronic components that are mounted on the wiring substrate. The wiring substrate has component mounting regions, wherein at least one electronic component is mounted in each of the component mounting regions, and component non-mounting regions, wherein no electronic component is mounted in each of the component non-mounting regions. The component mounting regions and the component non-mounting regions are provided alternately in a longitudinal direction of the wiring substrate. The component non-mounting regions are curved along an outer circumferential direction of the ring-shaped member.

16 Claims, 6 Drawing Sheets (56) References Cited

FOREIGN PATENT DOCUMENTS

| | | | |
|---|---|---|---|
| JP | 2000-342547 | A | 12/2000 |
| JP | 2007-105316 | | 4/2007 |
| JP | 2008-099890 | A | 5/2008 |
| JP | 2008-279061 | A | 11/2008 |
| JP | 2012-134272 | A | 7/2012 |
| WO | 2014/087843 | A1 | 6/2014 |

* cited by examiner

SEMICONDUCTOR DEVICE AND SENSOR MODULE

This application claims priority from Japanese Patent Applications No. 2018-081119 filed on Apr. 20, 2018, the entire contents of which are herein incorporated by reference.

BACKGROUND

1. Technical Field

The present disclosure relates to a semiconductor device and a sensor module.

2. Background Art

Various sensor modules for detecting various vital sign information from a human body have been developed. As an example of such a sensor module, there is a pulse oximeter in which a probe provided with a light emitting element and a light receiving element is worn on a finger of an examinee to project light toward the finger to thereby measure a change of a light quantity of the light via the finger so that a temporal change of blood oxygen saturation can be obtained by a control circuit including a CPU (e.g. see JP-A-2007-105316).

However, in the background-art sensor module, electronic components used for measurement including the light emitting element, the light receiving element and the control circuit cannot be mounted on a single wiring substrate so as to be worn on a fingertip. Meanwhile, the electronic components can be worn on an entire finger including the fingertip.

The present disclosure has been accomplished in consideration of the aforementioned point. An object of the present disclosure is to provide a sensor module in which electronic components used for measurement can be mounted on a single wiring substrate so as to be worn on a fingertip comfortably.

SUMMARY

Certain embodiments provide a sensor module.
The sensor module comprises:
a ring-shaped member; and
a semiconductor device that is provided on the ring-shaped member, the semiconductor device comprising:
  a wiring substrate that has flexibility; and electronic components that are mounted on the wiring substrate,
wherein the wiring substrate has component mounting regions (M), wherein at least one electronic component is mounted in each of the component mounting regions, and component non-mounting regions, wherein no electronic component is mounted in each of the component non-mounting regions,
the component mounting regions and the component non-mounting regions are provided alternately in a longitudinal direction of the wiring substrate, and
the component non-mounting regions are curved along an outer circumferential direction of the ring-shaped member.
Certain embodiments provide a semiconductor device.
The semiconductor device comprises:
a wiring substrate that has flexibility; and
electronic components that are mounted on the wiring substrate,
wherein the wiring substrate has component mounting regions, wherein at least one electronic component is mounted in each of the component mounting regions, and component non-mounting regions, wherein no electronic component is mounted in each of the component non-mounting regions, and
the component mounting regions and the component non-mounting regions are provided alternately in a longitudinal direction of the wiring substrate.

DETAILED DESCRIPTION

The present disclosure will be described below with reference to the drawings. Incidentally, the same elements are designated with the same reference numbers in the respective drawings so that duplicated description of the same elements can be omitted.

First Embodiment

Semiconductor Device

Figure 1A:
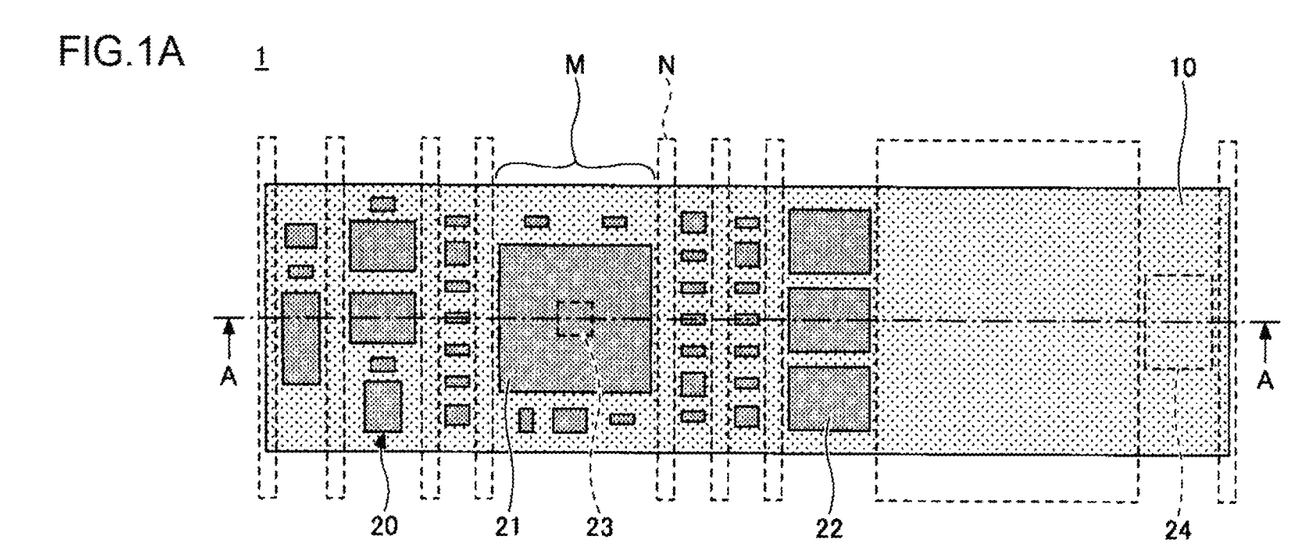
FIG. 1A is a plan view showing a semiconductor device according to a first embodiment.
Figure 1B:
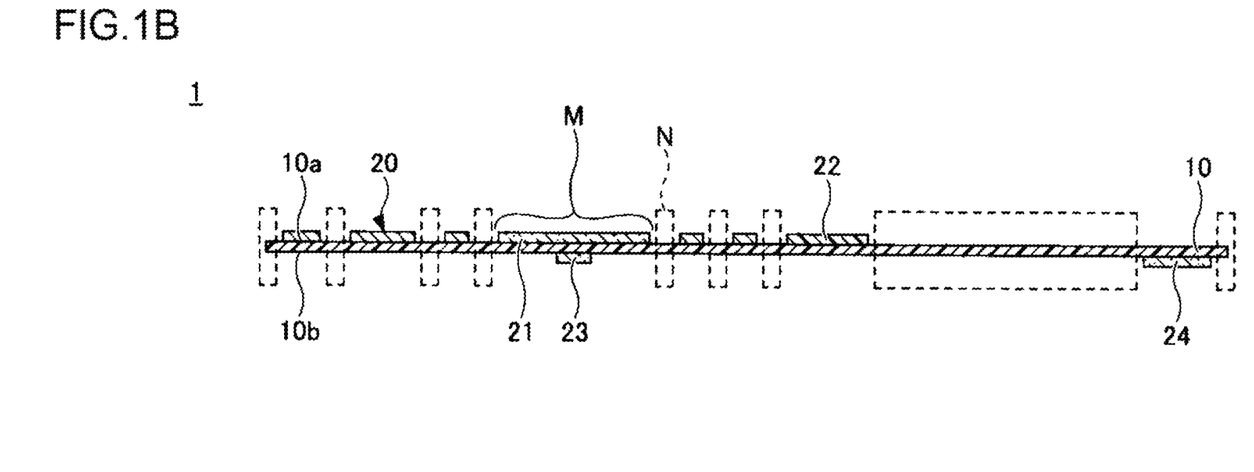
FIG. 1B is a sectional view showing the semiconductor device according to the first embodiment.

FIGS. 1A and 1B are views illustrating a semiconductor device according to a first embodiment. FIG. 1A is a plan view, and FIG. 1B is a sectional view taken along a line A-A of FIG. 1A.

As shown in FIGS. 1A and 1B, the semiconductor device 1 includes a wiring substrate 10 and electronic components 20.

Figure 2:
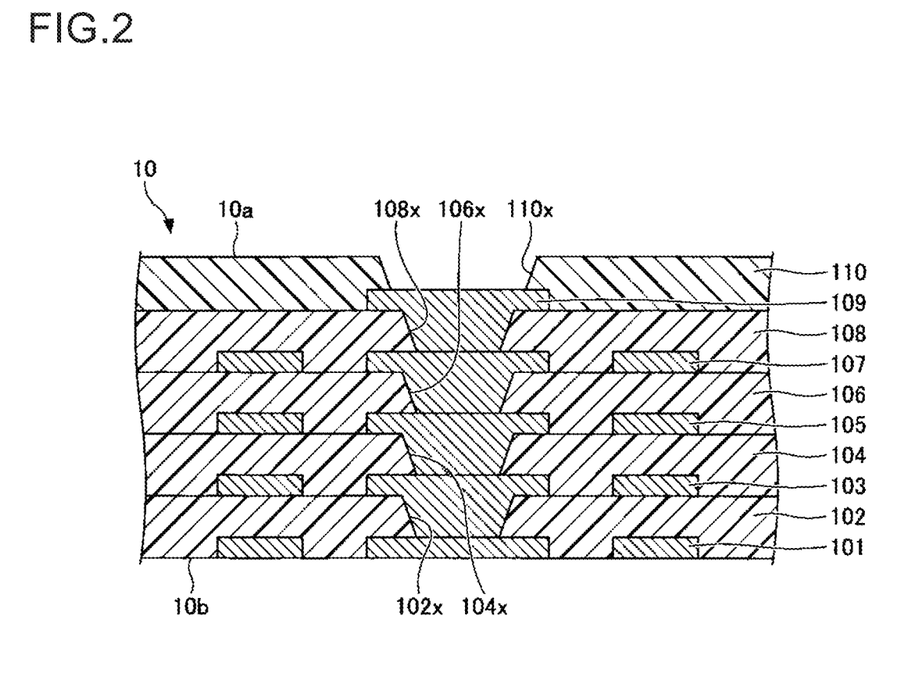
FIG. 2 is a sectional view illustrating a wiring substrate constituting the semiconductor device according to the first embodiment.

The wiring substrate 10 is a coreless substrate having flexibility. As shown in FIG. 2, the wiring substrate 10 is constituted by a multilayer (e.g. five-layer) structure in which wiring layers are formed on one another with interposition of an insulating layer between adjacent ones of the wiring layers. Here, the flexibility means a bendable or flexible property.

In an example of FIG. 2, the wiring substrate 10 is formed such that a wiring layer 101, an insulating layer 102, a wiring layer 103, an insulating layer 104, a wiring layer 105, an insulating layer 106, a wiring layer 107, an insulating layer 108, a wiring layer 109 and a solder resist layer 110 are sequentially formed on one another. The formation number of the wiring layers and the formation number of the insulating layers can be determined suitably if necessary.

Incidentally, a solder resist layer 110 side of the wiring substrate 10 will be regarded as upper side or one side, and a wiring layer 101 side of the wiring substrate 10 will be regarded as lower side or the other side for the sake of convenience in the present embodiment. In addition, a solder resist layer 110 side surface of each element will be regarded as one surface or upper surface and a wiring layer 101 side surface of each element will be regarded as the other surface or lower surface. Incidentally, the wiring substrate 10 can be used in an upside-down state or can be disposed at any angle. Moreover, the plan view means a view of an object seen from a normal direction to one surface 10a (an upper surface of the solder resist layer 110) of the wiring substrate 10, and a planar shape means a shape of the object seen from the normal direction to the one surface 10a (the upper surface of the solder resist layer 110) of the wiring substrate 10.

The wiring layer 101 is formed in a lowermost layer of the wiring substrate 10. The wiring layer 101 can be formed into a structure in which, for example, a gold (Au) film, a palladium (Pd) film, a nickel (Ni) film, and a copper (Cu) film are formed sequentially in the named order so that the gold (Au) film can come to the lower side. Incidentally, the palladium (Pd) film or the nickel (Ni) film may not be formed in the wiring layer 101.

A lower surface (a lower surface of the gold (Au) film in the aforementioned case) of the wiring layer 101 is exposed from a lower surface of the insulating layer 102. An upper surface (excluding each connection portion with the wiring layer 103) and side surfaces of the wiring layer 101 are covered with the insulating layer 102. The lower surface of the wiring layer 101 can be, for example, flush with the lower surface of the insulating layer 102. A thickness of the wiring layer 101 (the sum of thicknesses of the respective films constituting the wiring layer 101) can be, for example, about 10 μm to about 20 μm. The wiring layer 101 can be used as pads to be connected to terminals of the electronic components 20.

The insulating layer 102 is formed to cover the wiring layer 101. For example, an insulating resin having flexibility and a low Young's modulus (e.g. a thermosetting resin) can be used as a material of the insulating layer 102. For example, an insulating resin containing a polyimide-based resin, an epoxy-based resin, or the like, as a main component may be used as the insulating resin having the flexibility and the low Young's modulus. The insulating layer 102 can be, for example, about 20 μm to about 45 μm thick. The insulating layer 102 may contain a filler of silica ($SiO_2$) or the like.

The wiring layer 103 is formed on one side of the insulating layer 102 to be electrically connected to the wiring layer 101. The wiring layer 103 includes a via wiring with which each via hole 102x is filled, and a wiring pattern that is formed on one surface of the insulating layer 102. The via hole 102x penetrates the insulating layer 102 to expose one surface of the wiring layer 101. The via hole 102x is formed into a reverse truncated cone-shaped recess in which a diameter of an opening portion opened on an insulating layer 104 side is larger than the diameter of the bottom surface of the opening portion formed by the upper surface of the wiring layer 101. The diameter of the opening portion of the via hole 102x can be, for example, about 60 μm to about 70 μm.

For example, copper (Cu) or the like can be used as a material of the wiring layer 103. The wiring pattern constituting the wiring layer 103 can be, for example, about 10 μm to about 20 μm thick. The wiring layer 103 can be formed as micro wirings whose line and space (hereinafter shortened to "line/space") is about 10 μm/10 μm to about 20 μm/20 μm. Incidentally, the line and the space in the line/space express a wiring width and an interval between adjacent wirings (a wiring interval) respectively. For example, when the line/space is described as 10 μm/10 μm, it means that the wiring width is 10 μm and the interval between the adjacent wirings is 10 μm.

The insulating layer 104 is formed on the one surface of the insulating layer 102 to cover the wiring layer 103. A material or a thickness of the insulating layer 104 can be, for example, made similar to or the same as that of the insulating layer 102. The insulating layer 104 may contain a filler of silica ($SiO_2$) or the like.

The wiring layer 105 is formed on one side of the insulating layer 104 to be electrically connected to the wiring layer 103. The wiring layer 105 includes a via wiring with which each via hole 104x is filled, and a wiring pattern that is formed on one surface of the insulating layer 104. The via hole 104x penetrates the insulating layer 104 to expose one surface of the wiring layer 103. The via hole 104x is formed into a reverse truncated cone-shaped recess in which a diameter of an opening portion opened on an insulating layer 106 side is larger than the diameter of the bottom surface of the opening portion formed by the upper surface of the wiring layer 103. The diameter of the opening portion of the via hole 104x can be, for example, about 60 μm to about 70 μm. A material of the wiring layer 105 and a thickness or line/space of the wiring pattern constituting the wiring layer 105 can be, for example, made similar to or the same as those of the wiring layer 103.

The insulating layer 106 is formed on the one surface of the insulating layer 104 to cover the wiring layer 105. A material or a thickness of the insulating layer 106 can be, for example, made similar to or the same as that of the insulating layer 102. The insulating layer 106 may contain a filler of silica ($SiO_2$) or the like.

The wiring layer 107 is formed on one side of the insulating layer 106 to be electrically connected to the wiring layer 105. The wiring layer 107 includes a via wiring with which each via hole 106x is filled, and a wiring pattern that is formed on one surface of the insulating layer 106. The via hole 106x penetrates the insulating layer 106 to expose one surface of the wiring layer 105. The via hole 106x is formed into a reverse truncated cone-shaped recess in which a diameter of an opening portion opened on an insulating layer 108 side is larger than the diameter of the bottom surface of the opening portion formed by the upper surface of the wiring layer 105. The diameter of the opening portion of the via hole 106x can be, for example, about 60 μm to about 70 μm. A material of the wiring layer 107 and a thickness or line/space of the wiring pattern constituting the wiring layer 107 can be, for example, made similar to or the same as those of the wiring layer 103.

The insulating layer 108 is formed on the one surface of the insulating layer 106 to cover the wiring layer 107. A material or a thickness of the insulating layer 108 can be, for example, made similar to or the same as that of the insulating layer 102. The insulating layer 108 may contain a filler of silica ($SiO_2$) or the like.

The wiring layer 109 is formed on one side of the insulating layer 108 to be electrically connected to the wiring layer 107. The wiring layer 109 includes a via wiring with which each via hole 108x is filled, and a wiring pattern that is formed on one surface of the insulating layer 108. The via hole 108x penetrates the insulating layer 108 to expose one surface of the wiring layer 107. The via hole 108x is formed into a reverse truncated cone-shaped recess in which the diameter of an opening portion opened on a solder resist layer 110 side is larger than the diameter of the bottom surface of the opening portion formed by the upper surface of the wiring layer 107. The diameter of the opening portion of the via hole 108x can be, for example, about 60 μm to about 70 μm. A material of the wiring layer 109 and a thickness or line/space of the wiring pattern constituting the wiring layer 109 can be, for example, made similar to or the same as those of the wiring layer 103.

The solder resist layer 110 is formed on the one surface of the insulating layer 108 to cover the wiring layer 109. The solder resist layer 110 can be, for example, formed from a photosensitive resin such as an epoxy-based resin or an acrylic-based resin etc. The solder resist layer 110 can be, for example, about 15 μm to about 35 μm thick.

The solder resist layer 110 has opening portions 110x. Portions of an upper surface of the wiring layer 109 are exposed inside the opening portions 110x. A planar shape of each of the opening portions 110x can be, for example, formed into a circle. If necessary, a metal layer may be formed on the upper surface of the wiring layer 109 exposed inside the opening portions 110x or anti-oxidation treatment such as OSP (Organic Solderability Preservative) treatment may be applied to the upper surface of the wiring layer 109. As examples of the metal layer, an Au layer, Ni/Au layers (a metal layer in which an Ni layer and an Au layer are formed in the named order), Ni/Pd/Au layers (a metal layer in which an Ni layer, a Pd layer and an Au layer are formed in the named order), etc. can be used.

The wiring layer 109 exposed inside the opening portions 110x can be used as pads to be connected to terminals of the electronic components 20 or as pads for checking signal waveforms.

In the wiring substrate 10, the upper surface of each of the wiring layers disposed on each of the via wirings is not recessed but flat. Accordingly, a stack via structure in which the via wirings are stacked on one another vertically can be attained in the wiring substrate 10, as shown in FIG. 2. Thus, it is possible to improve density of the wiring layers of the wiring substrate 10, and it is possible to improve reliability of electrical connection through the via wirings among the wiring layers. However, the wiring substrate 10 may take a form in which such a stack via structure is not provided.

Return to description of FIGS. 1A and 1B. Electronic components 20 are mounted on each of the one surface 10a (the upper surface of the solder resist layer 110) and the other surface 10b (the lower surface of the insulating layer 102) of the wiring substrate 10.

The electronic components 20 include semiconductor components and passive components. For example, a CPU (Central Processing Unit), an ROM (Read Only Memory), an RAM (Random Access Memory), an LED (Light Emitting Diode), a PD (Photo Diode), etc. can be used as the semiconductor components. For example, a resistor, a capacitor, an inductor, an antenna, a connector, etc. can be used as the passive components. Incidentally, the antenna may be mounted as an electronic component or may be formed by a wiring pattern. Incidentally, although a CPU 21 is illustrated as an example of a processor in the present embodiment, a GPU, an MPU, an FPGA or an ASIC may be used as the processor in place of the CPU 21.

Of the electronic components 20, only main components will be designated with numeral references in the description. For example, the semiconductor device 1 is provided with the CPU 21, a connector 22, an LED 23, and a PD 24 and has a function of acquiring predetermined information from a measurement object. The CPU 21 controls the semiconductor device 1 as a whole. The CPU 21 is an electronic component whose area in plan view is largest among the electronic components 20 mounted on the semiconductor device 1. The connector 22 serves as a terminal through which power to be supplied to the CPU 21 etc. is inputted from the outside. The LED 23 is a light emitting element that is controlled by the CPU 21 to emit light (e.g. red light or infrared light) with a predetermined wavelength range to the measurement object. The PD 24 is a light receiving element that receives reflected light or transmitted light of the emitted light of the LED 23 from or through the measurement object, converts the received reflected light or the received transmitted light into an electric signal, and delivers the converted electric signal to the CPU 21.

In the example of FIGS. 1A and 1B, the CPU 21 and the connector 22 are mounted on the one surface 10a of the wiring substrate 10. In addition, the LED 23 and the PD 24 are mounted on the other surface 10b of the wiring substrate 10. The LED 23 can be, for example, mounted to be opposed to the CPU 21 with interposition of the wiring substrate 10 therebetween.

Component mounting regions M and component non-mounting regions N (regions each of which is enclosed by a broken line in FIGS. 1A and 1B) are disposed alternately in a longitudinal direction of the semiconductor device 1 on the semiconductor device 1. The electronic components 20 are mounted on the wiring substrate 10 in the component mounting regions M. None of the electronic components 20 is mounted on the wiring substrate 10 in the component non-mounting regions N.

The semiconductor device 1 is designed such that the semiconductor device 1 is bent at longitudinally arranged places and deformed into a ring shape in use. In the semiconductor device 1, the component mounting regions M and the component non-mounting regions N are disposed alternately. Thus, the respective component non-mounting regions N can be bent and easily deformed into the ring shape.

In addition, it is preferable that electronic components 20 are arranged in one row in a lateral direction of semiconductor device 1 in each of all or some of the component mounting regions M. Thus, the width of the component mounting region M can be narrowed so that the semiconductor device 1 can be easily deformed into the ring shape.

Incidentally, the wiring patterns constituting the respective wiring layers may be disposed in either the component mounting regions M or the component non-mounting regions N. However, the via wirings (e.g. the stacked vias shown in FIG. 2) are disposed in only the component mounting regions M. Since the via wirings are disposed in only the component mounting regions M that cannot bend at all or can hardly bend, the via wirings can be prevented from being cracked when the component non-mounting regions N are bent.

Sensor Module

Next, a sensor module 3 using such a semiconductor device 1 will be described. Here, a case where the sensor module 3 is a wearable device for measuring arterial oxygen saturation ($SPO_2$) will be described. However, this is merely an example. The sensor module 3 may measure any other measurement object than the arterial oxygen saturation. For example, a pulse rate or body temperature can be used as the other measurement object than the arterial oxygen saturation.

Figure 3:
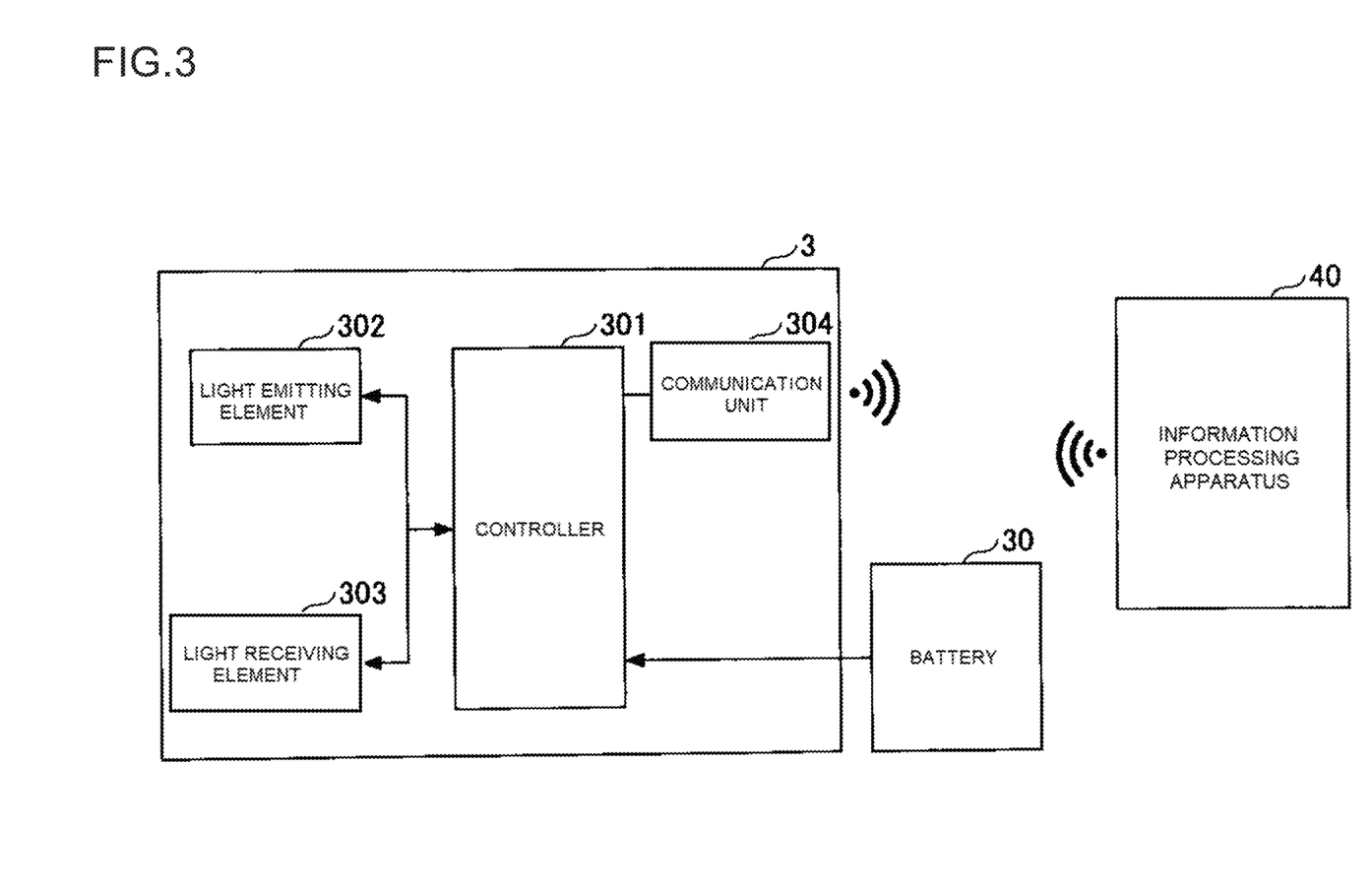
FIG. 3 is a diagram illustrating functional blocks of a sensor module according to the first embodiment.

FIG. 3 is a diagram illustrating functional blocks of the sensor module according to the first embodiment. As shown in FIG. 3, the sensor module 3 has a controller 301, a light emitting element 302, a light receiving element 303 and a communication unit 304 as the functional blocks. The sensor module 3 may have any other functional block if necessary.

The controller 301 may include a CPU 21, an ROM, an RAM, a main memory, etc. In this case, various functions of the controller 301 can be realized in such a manner that programs stored in the ROM are read by the main memory and executed by the CPU 21. However, the controller 301 may be realized by only hardware. The controller 301 can be activated with power supply from a battery 30 disposed outside the sensor module 3.

The light emitting element 302 has a function of emitting infrared light or red light in accordance with control of the controller 301. The light emitting element 302 can be realized, for example, by an LED 23 in which an IR LED and a RED LED are integrated into one chip. The IR LED is a light emitting diode that emits the infrared light. The RED LED is a light emitting diode that emits the red light.

The light receiving element 303 is configured to receive light transmitted through a measurement object from the light emitting element 302, and convert the received light into an electric signal. The light receiving element 303 can be, for example, realized by a photo diode (PD) 24. Information received by the light receiving element 303 and converted into an electric signal is sent to the CPU 21.

The communication unit 304 is configured to exchange information between the controller 301 and an information processing apparatus 40 disposed outside the sensor module 3 by wireless. The information processing apparatus 40 is, for example, a personal computer or a tablet terminal. The communication unit 304 can be, for example, realized by a not-shown communication device and a not-shown antenna. The communication unit 304 can transmit, to the information processing apparatus 40, for example, data of $SPO_2$ that have been calculated by the controller 301 based on an output of the light receiving element 303.

Measurement principles of the $SPO_2$ will be described. The $SPO_2$ is a value indicating the percentage of hemoglobin to which oxygen is bound, to hemoglobin contained in red blood cells flowing in blood (arterial blood) carried all over a body from a heart. When the hemoglobin is bound with the oxygen, the hemoglobin turns to a reddish color. When the hemoglobin is not bound with the oxygen, the hemoglobin turns to a blackish color. This means that the red light is easily transmitted through the hemoglobin bound with the oxygen and that a whole range of visible light including the red light is hardly transmitted through the hemoglobin not bound with the oxygen. Incidentally, irrespective of whether the hemoglobin is bound with the oxygen or not, the infrared light is easily transmitted through the hemoglobin.

Assume that the red light is radiated from the RED LED of the light emitting element 302 to a fingertip. In this case, when a large proportion of the hemoglobin is bound with the oxygen, a transmission ratio of the red light through the hemoglobin is high. Accordingly, an amount of the red light received by the light receiving element 303 is large. On the other hand, when a small proportion of the hemoglobin is bound with the oxygen, the transmission ratio of the red light through the hemoglobin is low. Accordingly, the amount of the red light received by the light receiving element 303 is small.

On the other hand, assume that the infrared light is radiated from the IR LED of the light emitting element 302 to the fingertip. In this case, irrespective of whether a proportion of the hemoglobin bound with the oxygen is large or not, a transmission ratio of the infrared light through the hemoglobin is high. Accordingly, an amount of the infrared light received by the light receiving element 303 is always large.

That is, the $SPO_2$ can be measured by obtaining a ratio between the amount of the red light received by the light receiving element 303 when the red light is radiated and the amount of the infrared light received by the light receiving element 303 when the infrared light is radiated. For example, the controller 301 can calculate the $SPO_2$ based on the ratio between the amount of the red light and the amount of the infrared light.

Figures 4A, 4B, 4C, 4D, 4E, 4F:
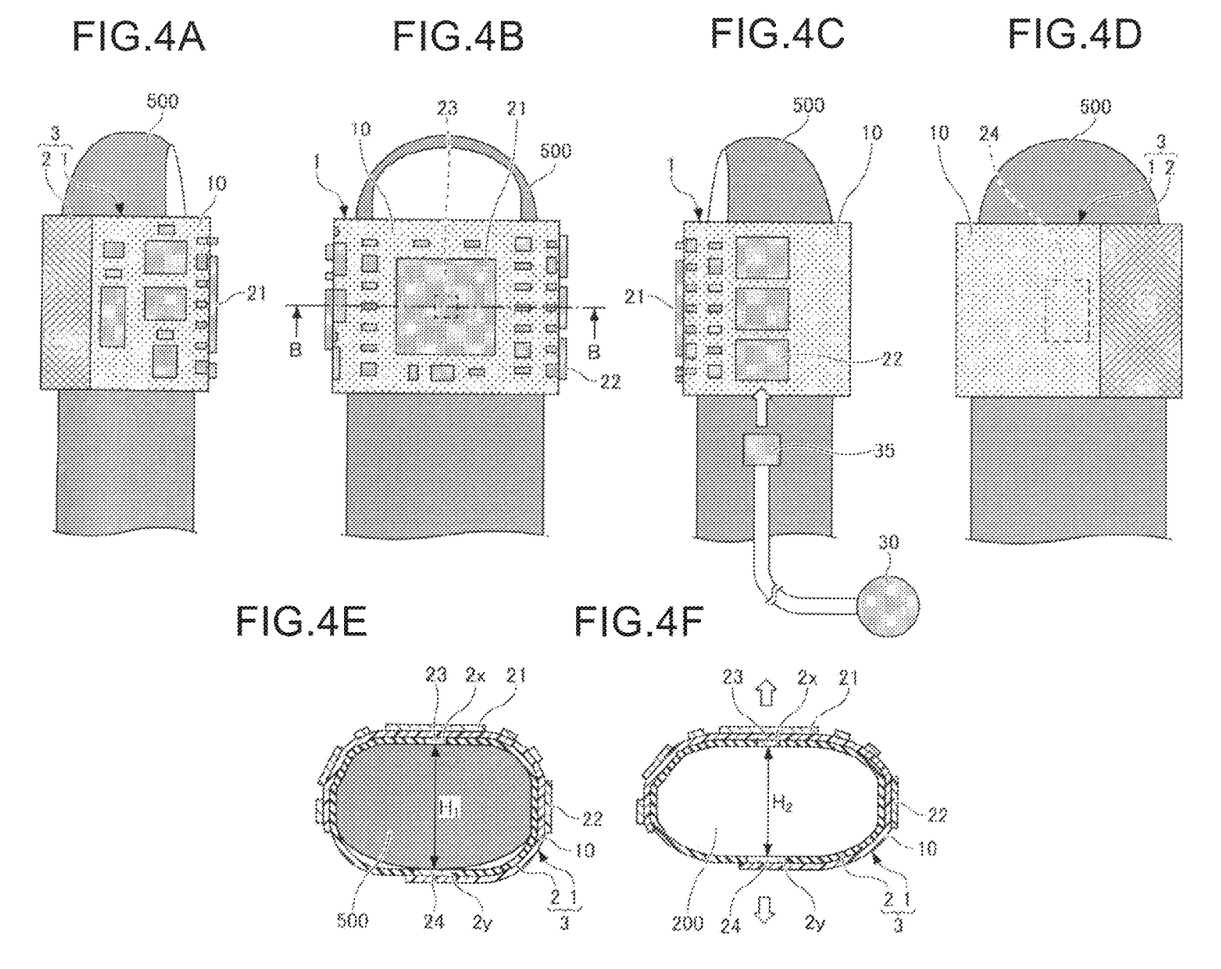
FIG. 4A is a left side view showing the sensor module that has been already mounted on a finger.
FIG. 4B is a plan view showing the sensor module that has been already mounted on the finger.
FIG. 4C is a right side view showing the sensor module that has been already mounted on the finger.
FIG. 4D is a bottom view showing the sensor module that has been already mounted on the finger.
FIG. 4E is a sectional view showing the sensor module that has been already mounted on the finger.
FIG. 4F is a sectional view showing the sensor module that has not been yet mounted on the finger.

FIGS. 4A to 4F are views for explaining the sensor module according to the first embodiment. FIGS. 4A to 4E show a state in which the sensor module 3 has been already mounted on a finger 500 that is a measurement object. FIG. 4B is a plan view of the sensor module 3 mounted on the finger 500. FIG. 4A is a left side view of the sensor module 3 mounted on the finger 500. FIG. 4C is a right side view of the sensor module 3 mounted on the finger 500. FIG. 4D is a bottom view of the sensor module 3 mounted on the finger 500. FIG. 4E is a sectional view of the sensor module 3 mounted on the finger 500, which is taken along a line B-B of FIG. 4B. FIG. 4F is a sectional view of the sensor module 3 mounted on the finger 500, which shows a state in which the sensor module 3 has not been yet mounted on the finger 500 that is the measurement object. FIG. 4F shows a section corresponding to that of FIG. 4E. Incidentally, a view of a palm of a hand seen from a nail side is regarded as the plan view here.

As shown in FIGS. 4A to 4F, the sensor module 3 has the semiconductor device 1 and a ring-shaped member 2. The ring shape means a closed annular shape that has a space portion at the center when seen from a predetermined direction. For example, the closed annular shape may be circular, elliptical, etc. As long as the closed annular shape has the space portion at the center when seen from the predetermined direction, the closed annular shape does not have to be circular or elliptical but may include, for example, a linear portion. In addition, the ring shape may also include a shape in which a portion of the closed annular shape is open (e.g. a shape approximating to an alphabet C). This will be described separately as a modification.

The semiconductor device 1 is fixedly bonded to an outer circumferential surface of the ring-shaped member 2 so that the CPU 21 can face the outside. The component non-mounting regions N (see FIGS. 1A and 1B) of the semiconductor device 1 are curved along the outer circumferential surface of the ring-shaped member 2. The semiconductor device 1 may be fixedly bonded to the entire outer circumferential surface of the ring-shaped member 2 or may be fixedly bonded to a portion of the outer circumferential surface of the ring-shaped member 2 as shown in FIG. 4E.

Figure 5:
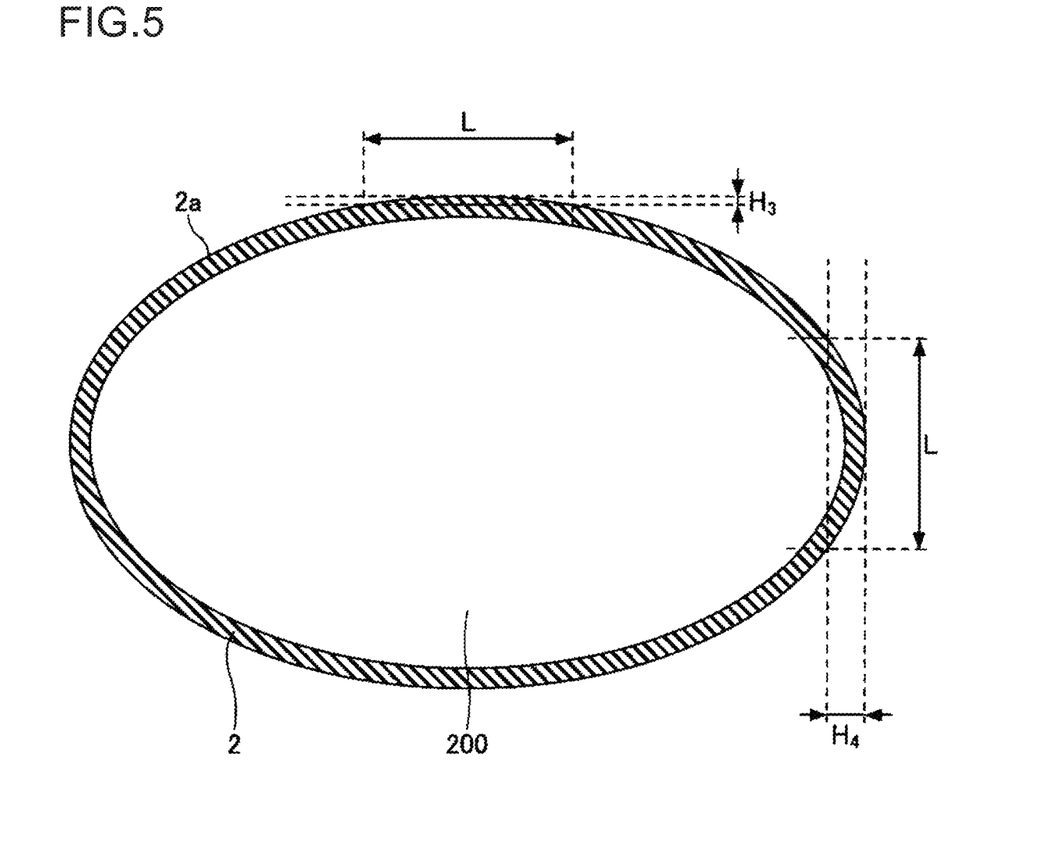
FIG. 5 is a view for explaining an aspect ratio of a ring-shaped member.

The ring-shaped member 2 is provided with high aspect ratio regions and low aspect ratio regions. The ring-shaped member 2 is designed on the assumption that the ring-shaped member 2 will be mounted on a human being's finger 500. Accordingly, a nail side (back side) of the finger 500 and a ball side of the finger 500 opposite thereto are regarded as relatively high aspect ratio regions according to the shape of the finger. Here, the aspect ratio is defined as L/H when a height H between a lowest point and a highest point of the outer circumferential surface of the ring-shaped member 2 has been obtained in a predetermined range L. For example, an aspect ratio of a region with a height $H_3$ shown in FIG. 5 is $L/H_3$, and an aspect ratio of a region with a height $H_4$ ($H_4 > H_3$) shown in FIG. 5 is $L/H_4$. The region with the height $H_3$ shown in FIG. 5 is a relatively high aspect ratio region, and the region with the height $H_4$ shown in FIG. 5 is a relatively low aspect ratio region. Incidentally, the high aspect ratio region is, for example, a region overlapping with the nail of the finger 500 in plan view.

The CPU 21 that is an electronic component whose area in plan view is largest among the electronic components 20 is mounted on an outer circumferential surface of the wiring substrate 10 positioned on the high aspect ratio region of the ring-shaped member 2. Thus, mounting efficiency can be improved.

In addition, the component mounting regions M (see FIGS. 1A and 1B) where the electronic components 20 are mounted cannot be bent at all or can be hardly bent. Therefore, when one of the component mounting regions M where the electronic component whose area in plan view is largest among the electronic components 20 is disposed on the high aspect ratio region of the ring-shaped member 2 that does not have to be bent largely, it is possible to ensure easiness of bending of the entire sensor module 3. In addition, the via wirings may be provided only in the high aspect ratio regions of the ring-shaped member 2 that do not have to be bent largely. Thus, the via wirings can be prevented from being cracked.

Incidentally, the electronic component whose area in plan view is largest among the electronic components 20 is regarded as the CPU 21 by way of example. The aforementioned effect can be obtained when the electronic component whose area in plan view is largest is mounted on the outer circumferential surface of the wiring substrate 10 positioned on the high aspect ratio region of the ring-shaped member 2.

The connector 22 is a terminal through which power to be supplied to the CPU 21 etc. is inputted from the outside. For example, the connector 22 is configured to receive a connector 35 connected to a battery 30 through a wire material etc. The battery 30 is, for example, a button type battery that can be mounted on a wrist etc. Incidentally, a special battery for the sensor module 3 may be used as the battery 30. However, when another sensor module than the sensor module 3 is worn on a human body, a battery shared with the other sensor module may be used.

Through holes 2x and 2y are provided in the ring-shaped member 2. The LED 23 mounted on the other surface 10b of the wiring substrate 10 is positioned inside the through hole 2x. An emission surface of the LED 23 is exposed to the outside from the through hole 2x and located in a position to contact the finger 500. In addition, the PD 24 mounted on the other surface 10b of the wiring substrate 10 is positioned inside the through hole 2y. An entrance surface of the PD 24 is exposed to the outside from the through hole 2y and located in a position to contact the finger 500.

The LED 23 is mounted on the other surface 10b of the wiring substrate 10 positioned on the high aspect ratio region. The PD 24 is mounted to be opposed to the LED 23 with interposition of the space portion 200 of the ring-shaped member 2 therebetween. Light emitted from the LED 23 can be transmitted through the finger 500 that has been inserted into the space portion 200 of the ring-shaped member 2, and then received by the PD 24.

As shown in FIG. 4F, it is preferable that a sectional shape of the sensor module 3 that has not been yet worn on the finger 500 is formed in advance with a height $H_2$ of the space portion 200 lower than a height $H_1$ (see FIG. 4E) of the finger 500 on which the sensor module 3 is assumed to be worn. In addition, it is preferable that the ring-shaped member 2 is formed out of a material having elasticity. Specific examples of the material having elasticity and used for the ring-shaped member 2 include urethane rubber, acrylic rubber, silicone, etc. The elasticity means restoration capability of the material to an initial state after the material is elastically deformed.

The height $H_2$ is formed to be lower than the height $H_1$ and the ring-shaped member 2 has elasticity. Accordingly, even if the height $H_1$ varies, the sensor module 3 can extend in an arrow direction (height direction) of FIG. 4F due to the elasticity of the ring-shaped member 2 when the sensor module 3 is worn on the finger 500. As a result, the emission surface of the LED 23 and the entrance surface of the PD 24 can be surely brought into contact with the finger 500 so that an amount of light received by the PD 24 can increase. Accordingly, measurement accuracy can be improved.

In addition, it is preferable that the ring-shaped member 2 is formed out of a material having a known dielectric constant. When the ring-shaped member 2 is formed out of the material having the known dielectric constant, the antenna can be designed easily.

In the semiconductor device 1 constituting the sensor module 3, the electronic components 20 are mounted with high density on the wiring substrate 10 of the multilayer structure provided with the micro wirings. Therefore, even when the electronic components used for measurement including the light emitting element, the light receiving element and the control circuit are mounted on a single wiring substrate 10, the sensor module 3 can be miniaturized. In addition, in the semiconductor device 1 constituting the sensor module 3, the component mounting regions M and the component non-mounting regions N are disposed alternately. Therefore, the component non-mounting regions N can be bent in accordance with the shape of the finger to be thereby formed into the ring type easily.

That is, the sensor module 3 is so small in size and so easy to bend that the sensor module 3 can be formed into the ring shape easily. Therefore, the sensor module 3 does not have to be worn on the entire finger as in the background art, but can be worn on only the fingertip comfortably. For example, the sensor module 3 is worn on only the fingertip anterior to a first joint of the finger. Thus, the finger can be bent easily even after the sensor module 3 is worn on the finger. Accordingly, a wearable device that can be worn with less discomfort feeling can be realized.

In addition, due to the antenna mounted on the wiring substrate 10, the sensor module 3 can make communication with the external information processing apparatus 40 by wireless. Therefore, it is possible to realize a wearable device that can be worn with less discomfort feeling than that in a case where the sensor module 3 makes communication with the external information processing apparatus 40 by wire.

First Modification of First Embodiment

An example in which the layout of some of the electronic components mounted on the wiring substrate of the semiconductor device is different from that according to the first embodiment will be shown in the first modification of the first embodiment. Incidentally, description about the same elements as those according to the aforementioned embodiment may be omitted in the first modification of the first embodiment.

Figure 6:
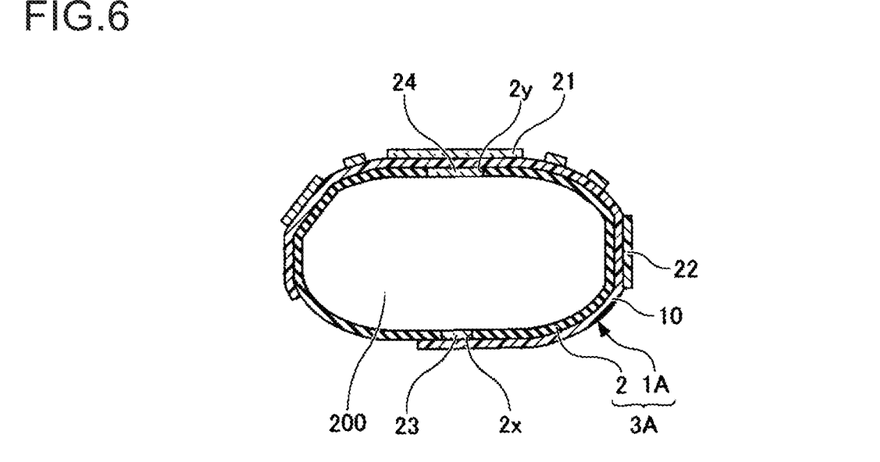
FIG. 6 is a view for explaining a sensor module according to the first modification of the first embodiment.

FIG. 6 is a view for explaining a sensor module according to the first modification of the first embodiment. FIG. 6 shows a sectional view in which the sensor module has not been yet worn on a finger.

The sensor module 3A shown in FIG. 6 is different from the sensor module 3 (see FIG. 4F) in that the semiconductor device 1 is replaced with a semiconductor device 1A. The semiconductor device 1A is different from the semiconductor device 1 in that an LED 23 and a PD 24 are mounted at opposite positions to those of the LED 23 and the PD 24 of the semiconductor device 1 respectively. That is, the PD 24 is mounted at the position opposite to a CPU 21 with interposition of a wiring substrate 10 therebetween, and the LED 23 is mounted at the position opposite to the PD 24 with interposition of a space portion 200 of a ring-shaped member 2 therebetween. Even in such a layout, light emitted from the LED 23 can be transmitted through a finger that has been inserted into the space portion 200 of the ring-shaped member 2, and then received by the PD 24.

An output of the PD 24 is an analog signal easily affected by external noise. Since the PD 24 is mounted at the position opposite to the CPU 21 with the interposition of the wiring substrate 10 therebetween, a wiring length of a wiring pattern connecting the PD 24 and the CPU 21 to each other can be shortened. Accordingly, the analog signal outputted by the PD 24 can be hardly affected by the noise. As a result, measurement accuracy of the sensor module 3A can be improved.

Second Modification of First Embodiment

An example in which a shape of a ring-shaped member is different from that according to the first embodiment will be shown in the second modification of the first embodiment. Incidentally, description about the same elements as those according to the aforementioned embodiment may be omitted in the second modification of the first embodiment.

Figure 7:
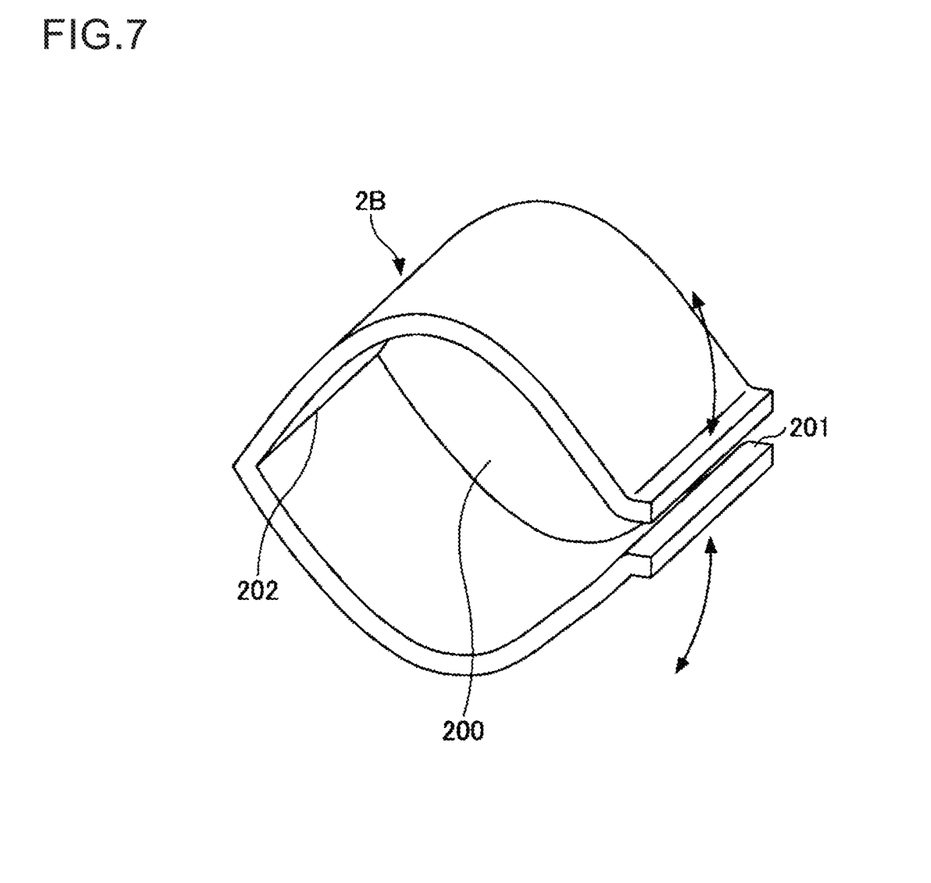
FIG. 7 is a perspective view showing another example of the ring-shaped member used in the sensor module.

FIG. 7 is a perspective view showing another example of a ring-shaped member used for a sensor module. The ring-shaped member 2B shown in FIG. 7 is an example of a shape in which a portion of a closed annular shape is open. An open portion 201 is provided on a side of the ring-shaped member 2B so that the ring-shaped member 2B can approximate to an alphabet C. In addition, a bent portion 202 is provided at a position opposite to the open portion 201 with interposition of a space portion 200 therebetween.

Thus, the ring-shaped member 2B is substantially formed into the C-shape having the open portion 201 and the bent portion 202. Thus, the open portion 201 of the ring-shaped member 2B can be easily moved back and forth in an arrow direction with the bent portion 202 as a fulcrum. Accordingly, the sensor module can be easily worn on a finger.

Although the preferred embodiment etc. has been described above in detail, the present disclosure is not limited to the aforementioned embodiment etc. but various modifications or replacements can be made on the aforementioned embodiment etc. without departing from the scope stated in claims.

What is claimed is:

1. A sensor module comprising:
   a ring-shaped member adapted to be worn on a human finger with a region of the ring-shaped member adapted to overlap a nail of the human finger when the ring-shaped member is worn on the human finger; and
   a semiconductor device that is provided on the ring-shaped member, the semiconductor device comprising:
      a wiring substrate that has flexibility; and electronic components that are mounted on the wiring substrate,
   wherein the wiring substrate has component mounting regions, wherein at least one electronic component is mounted in each of the component mounting regions, and component non-mounting regions, wherein no electronic component is mounted in each of the component non-mounting regions,
   the component mounting regions and the component non-mounting regions are provided alternately in a longitudinal direction of the wiring substrate,
   the component non-mounting regions are curved along an outer circumferential direction of the ring-shaped member, and
   an electronic component whose area in plan view is largest among the electronic components is mounted on one of the component mounting regions which is opposed to the region of the ring-shaped member overlapping the nail of the human finger.

2. The sensor module according to claim 1, wherein:
   the wiring substrate is a multilayer wiring substrate comprising:
      wiring layers;
      insulating layers each covering at least one of the wiring layers; and
      via wirings each formed in one of the insulating layers;
   each of the via wirings electrically connects two of the wiring layers which are adjacent to each other in a thickness direction of the wiring substrate, and
   the via wirings are disposed only in the component mounting regions.

3. The sensor module according to claim 1, wherein:
   the ring-shaped member has a high aspect ratio region and a low aspect ratio region lower in aspect ratio than the high aspect ratio region, the high aspect ratio region including the region of the ring-shaped member adapted to overlap the nail of the human finger; and
   the electronic component whose area in plan view is largest among the electronic components is mounted on one of the component mounting regions which is opposed to the high aspect ratio region.

4. The sensor module according to claim 3, wherein the largest electronic component is a processor.

5. The sensor module according to claim 3, wherein:
   the electronic components comprise a light emitting element that is configured to emit light, and a light receiving element that is configured to receive the light emitted from the light emitting element;
   the high aspect ratio region has a first high aspect ratio region and a second high aspect ratio region opposed to the first high aspect ratio region, the first high aspect ratio region being the region of the ring-shaped member adapted to overlap the nail of the human finger, and the second high aspect ratio region being a region of the ring-shaped member adapted to overlap a ball of the human finger, which is opposite to the nail of the human finger, when the ring-shaped member is worn on the human finger;
   the light emitting element is mounted on a first component mounting region of the component mounting regions which is opposed to the first high aspect ratio region; and the light receiving element is mounted on a second component mounting region of the component mounting regions which is opposed to the second high aspect ratio region.

6. The sensor module according to claim 5, wherein:
the first high aspect ratio region has a first through hole;
the second high aspect ratio region has a second through hole opposed to the first through hole;
an emission surface of the light emitting element is exposed through the first through hole; and
an entrance surface of the light receiving element is exposed through the second through hole.

7. The sensor module according to claim 5, wherein:
the ring-shaped member has an elliptical shape and a minor axis of the elliptical shape intersects the region of the ring-shaped member adapted to overlap the nail of the human finger and the region of the ring-shaped member adapted to overlap a ball of the human finger.

8. The sensor module according to claim 3, wherein:
the wiring substrate is a multilayer wiring substrate comprising:
wiring layers;
insulating layers each covering at least one of the wiring layers; and
via wirings each formed in one of the insulating layers;
each of the via wirings electrically connects two of the wiring layers which are adjacent to each other in a thickness direction of the wiring substrate, and
the via wirings are disposed only in the high aspect ratio region.

9. The sensor module according to claim 3, wherein:
the ring-shaped member has an elliptical shape and a minor axis of the elliptical shape intersects the region of the ring-shaped member adapted to overlap the nail of the human finger.

10. The sensor module according to claim 1, wherein some of the electronic components are arranged in a lateral direction of the wiring substrate in at least one of the component mounting regions.

11. The sensor module according to claim 1, wherein the ring-shaped member has elasticity.

12. The sensor module according to claim 1, wherein:
the ring-shaped member has an elliptical shape and a minor axis of the elliptical shape intersects the region of the ring-shaped member adapted to overlap the nail of the human finger.

13. The sensor module according to claim 1, wherein:
the wiring substrate is rectangular shaped with two opposite surfaces with rectangular shapes;
the electronic components are mounted on at least one of the opposite surfaces of the wiring substrate;
the component mounting regions and the component non-mounting regions are on the at least one of the opposite surfaces of the wiring substrate;
the component mounting regions and the component non-mounting regions respectively extend an entire width of the at least one of the opposite surfaces of the wiring substrate in a width direction orthogonal to the longitudinal direction, and the component non-mounting regions are bendable along an axis parallel to the width direction, and the component mounting regions are substantially unbendable along the axis parallel to the width direction, so that the semiconductor device is capable of curving by bending the component non-mounting regions along the axis parallel to the width direction.

14. A semiconductor device comprising:
a wiring substrate that has flexibility, the wiring substrate being rectangular shaped with two opposite surfaces with rectangular shapes; and
electronic components that are mounted on at least one of the opposite surfaces of the wiring substrate,
wherein the wiring substrate has component mounting regions on the at least one of the opposite surfaces, wherein at least one electronic component is mounted in each of the component mounting regions, and component non-mounting regions on the at least one of the opposite surfaces, wherein no electronic component is mounted in each of the component non-mounting regions,
the component mounting regions and the component non-mounting regions are provided alternately in a longitudinal direction of the wiring substrate, and respectively extend an entire width of the at least one of the opposite surfaces of the wiring substrate in a width direction orthogonal to the longitudinal direction, and
the component non-mounting regions are bendable along an axis parallel to the width direction, and the component mounting regions are substantially unbendable along the axis parallel to the width direction, so that the semiconductor device is capable of curving by bending the component non-mounting regions along the axis parallel to the width direction.

15. The semiconductor device according to claim 14, wherein the wiring substrate is a multilayer wiring substrate comprising:
wiring layers;
insulating layers each covering at least one of the wiring layers; and
via wirings each formed in one of the insulating layers,
wherein each of the via wirings electrically connects two of the wiring layers which are adjacent to each other in a thickness direction of the wiring substrate, and
the via wirings are disposed only in the component mounting regions.

16. The semiconductor device according to claim 14, wherein the wiring substrate is configured to be provided on a ring-shaped member, the ring-shaped member is adapted to be worn on a human finger with a region of the ring-shaped member adapted to overlap a nail of the human finger when the ring-shaped member is worn on the human finger, and the wiring substrate is configured to be provided on the ring-shaped member so that an electronic component whose area in plan view is largest among the electronic components is mounted on one of the component mounting regions which is opposed to the region of the ring-shaped member overlapping the nail of the human finger.

* * * * *